United States Patent [19]

Miyashita et al.

[11] Patent Number: 5,242,912
[45] Date of Patent: Sep. 7, 1993

[54] CYCLIC ANTHRANILIC ACID DERIVATIVES AND PROCESS OF PREPARING THE SAME

[75] Inventors: Mitsutomo Miyashita, Okaya; Yasushi Kohno, Oyama; Eisuke Kojima, Koga; Koji Saito, Oyama, all of Japan

[73] Assignee: Kyorin Pharmaceutical Co., Ltd., Tokyo, Japan

[21] Appl. No.: 674,343

[22] PCT Filed: Jun. 25, 1990

[86] PCT No.: PCT/JP90/00823
§ 371 Date: Apr. 25, 1991
§ 102(e) Date: Apr. 25, 1991

[87] PCT Pub. No.: WO91/00273
PCT Pub. Date: Jan. 10, 1991

[30] Foreign Application Priority Data

Jun. 26, 1989 [JP] Japan .................. 1-163145

[51] Int. Cl.$^5$ .................. C07D 513/00; A61K 31/55; A61K 31/38; A61K 31/335
[52] U.S. Cl. .................. 514/183; 514/211; 514/213; 514/431; 514/456; 540/468; 540/476; 540/552; 540/593
[58] Field of Search ........... 540/476, 468, 552, 593; 514/183, 211, 213, 431, 450

[56] References Cited

U.S. PATENT DOCUMENTS 3,794,646  2/1974  Welstead, Jr. et al. ............ 540/496
3,941,806  3/1976  Welstead, Jr. et al. ............ 548/490
4,935,511  6/1990  Youssofyeh et al. ............... 540/552

FOREIGN PATENT DOCUMENTS 0310096  4/1989  European Pat. Off. .
464827  11/1971  Japan .
62-23828  10/1987  Japan .

OTHER PUBLICATIONS

Meyers et al. J. Org. Chem. (1981) vol. 46 pp. 783-788.

Primary Examiner—Mukund J. Shah
Assistant Examiner—Matthew V. Grumbling
Attorney, Agent, or Firm—Oblon, Spivak, McClelland, Maier & Neustadt

[57] ABSTRACT

The following cyclic anthranilic acid derivative, their acid addition salts or alkali salts thereof represented by a general formula [I] are useful for antirheumatic drug, autoimmune disease curing drug and metabolic bone disease curing drug.

wherein $R^1$ to $R^6$ and X are as defined in claim 1.

2 Claims, No Drawings

CYCLIC ANTHRANILIC ACID DERIVATIVES AND PROCESS OF PREPARING THE SAME

FIELD OF THE TECHNIQUE

The present invention concerns novel cyclic anthranilic acid derivatives, their acid addition salts or alkali salts which have immuno-modulating action and strong inducing ability of suppressor T-cell as well as curing effect to rheumatic arthritis, preparing process thereof, and antirheumatic drug and immunodisease curing drug containing them as an active ingredient.

BACKGROUND OF THE TECHNIQUE

Chronic diseases related to immune responses include rheumatoid arthritis and other autoimmune diseases (systemic lupus erychematosus, psoriatic arthritis, atopic dermatitis, ankylosing spondylitis). These diseases are considered to be caused by bacteria, virus or autoantigens or by an aberration in cytokine regulation of T cells. Especially, patients with rheumatoid arthritis demonstrate various immune abnormalities including reduced functions of suppressor T cells and hyperactivity of B cells.

Non-steroidal antiinflammatory drugs are widely used as first choice drugs in the therapy of rheumatoid arthritis and other diseases due to immunological disorders. While these drugs offer symptomatic relief for patients with these diseases, they fail to alter the underlying immunological dysfunction or the overall course of the disease process. Furthermore, serious side effects from prolonged use of these drugs also have been well documented.

On the other hand, second choice antirheumatic drugs, such as gold salt and D-penicillamine have little acute antiinflammatory effects, but they appear to slow or halt the tissue destruction and more especially the progression of articular damage. They also have immunomodulatory effects. However, it is necessary to improve the safety and other aspects of these drugs, because of the higher incidence of side effects that have been observed in 40-50% of the patients treated with these drugs.

Metabolic bone diseases as generic term include osteoporosis, osteomalacia and ostetic fibrous. In patients with the diseases, there are morbid changes in weight, constitution and structure of bone as a result of the failure of the systemic bone formation and resorption process. This is caused by abnormalities in the somatological regulatory system due to various hormones or vitamins and by congenital or acquired abnormalities of the functions of the osteocytes. It is also associated with abnormal calcium and phosphorus metabolism. Vitamin D, calcium, calcitonin and phosphorus are used as therapeutic drugs, but their effectiveness has not been clearly proven and development of a superior drug has been strongly desired.

DISCLOSURE OF INVENTION

As the result of earnest investigations on the development of antirheumatism agent, the inventors of the present invention have found that the novel cyclic anthranilic acid derivatives, their acid addition salts or alkali salts represented by a general formula [I] of a category different from the known drugs have immuno-modulating action and strong inducing ability of suppressor T-cell, and further have excellent curing effect to rheumatic arthritis and high safety condition.

Furthermore, the inventors of the present invention have found that the compounds of the present invention have inhibitory action against destruction of bone, which has led to the completion of the present invention.

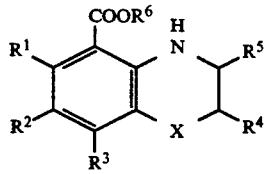

[I]

wherein $R^1$, $R^2$ or $R^3$, being same or different each other, denotes hydrogen atom, halogen atom, lower alkyl group of carbon number 1-3, lower alkoxy group of carbon number 1-3, amino group, nitro group, hydroxyl group, sulfonamide group, trifluoromethyl group, cyano group, carboxyl group, carbamoyl group, acetyl group, benzoylmethyl group which may be substituted, methylthio group, phenylethynyl group which can be substituted, ethynyl group which may be substituted, lower alkanoylamino group of carbon number 1-3, benzoylamino group which may be substituted, lower alkylsulfonylamino group of carbon number 1-3 or phenylsulfonylamino group which can be substituted respectively, $R^4$ or $R^5$, being same or different, denotes hydrogen atom, lower alkyl group of carbon number 1-3, cyano group, carboxyl group, hydroxymethyl group, phenyl group which can be substituted or benzyl group which can be substituted, respectively, $R^6$ denotes hydrogen atom, lower alkyl group of carbon number 1-3 or benzyl group x denotes single bond or denotes $-CHR^7-CHR^8-(CHR^9)m-$, $-O-CHR^8-(CHR^9)m-$, $-S(O)n-CHR^8-(CHR^9)m-$ or $-CO(CHR^8)p-(CHR^9)m-$ respectively, herein $R^7$, $R^8$ or $R^9$, being same or different each other, denotes hydrogen atom, lower alkyl group of carbon number 1-3, cyano group, carboxyl group, hydroxymethyl group, phenyl group which can be substituted, respectively, m or p denotes 0 or 1 respectively, and n denotes an integer of 0-2, provided $R^2$ can not be chlorine atom or hydrogen atom in case both $R^7$ and $R^8$ are hydrogen atom and m is equal to 0.

Besides, as the lower alkyl of lower alkyl group, lower alkoxy group, lower alkanoyl group, lower alkylsulfonylamino group etc., those of carbon number 1-3 of straight chain or branched chain such as for example methyl, ethyl, n-propyl, iso-propyl etc. can be exemplified. Further as the halogen atom, for example fluorine, chlorine, bromine or iodine can be exemplified. As "the phenyl which can be substituted" in benzoylmethyl group which can be substituted, phenylsulfonylamino group which can be substituted, benzoylamino group which can be substituted, phenylethynyl group which can be substituted and so on, those having one to three halogen atoms, lower alkyl group, lower alkoxy group or hydroxyl group at optional position on the benzen ring thereof can be exemplified.

Next, the processes for preparing the compound of the present invention are explained as follows. The so-called cyclic anthranilic acid has been synthesized by a process of oxidizing 1,7-trimethyleneisatin compounds with hydrogen peroxide in alkali (E. Ziegler et al., Monatsh. Chem., 94, 698 (1963), ibid 95, 59 (1964), U.S. Pat.

No. 3,794,646) and by other processes such as reduction or cyclization reaction of quinoline-8-carboxylic acid (C. Satyendranath et al., J. Annamalai Univ., 2, 227 (1933), L. S. Povarov et al., Izv. Akad. Naak SSSR, Serkhim, 144 (1966), C. G. Wad et al., J, Heterocycl. Chem., 2, 414 (1965)). However, in any case of them, only extremely restricted compounds are known and no report on pharmacological activities thereof has been recognized.

According to the present invention, a compound represented by the general formula [I] can be prepared through the following route.

Firstly, a compound of the general formula [I] wherein $R^6$ is hydrogen, i.e. a compound represented by a general formula [III] can be prepared by oxidizing a compound represented by a general formula [II] after alkali-treatment thereof. Typically speaking, it can be prepared by hydrolizing the compound represented by the general formula [II] with adding somewhat excess amount of a suitable base, for example, aqueous solution of sodium hydroxide or potassium hydroxide in a suitable solvent, for example, water or alcohol containing water, followed by oxidation thereof with not less than equimolecular amount of a mild oxidant, for example, aqueous solution of hydrogen peroxide or peracetic acid etc. It is preferable that the reaction temperature is 0°–50° C. and the reaction period is 30 minutes to 3 hours.

In case X represents —S—$CHR^8$—$(CHR^9)m$— in the general formula [II], a compound wherein S remains S, that wherein S changes to sulfinyl group and that wherein S changes to sulfonyl group, respectively, can be predominantly produced by controlling added amount of the oxidant and the working temperature. A compound of the general formula [II] which is a starting compound for the present process of preparation can be easily produced by a process similar to that of Japanese Kokai Sho 60-243088.

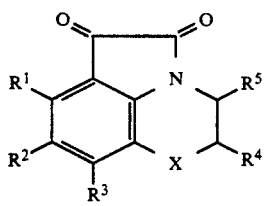

[II]

wherein $R^1$, $R^2$, $R^3$, $R^4$, $R^5$ and X are as above-mentioned.

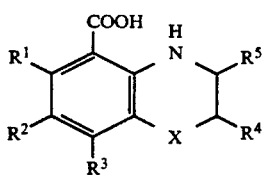

[III]

wherein $R^1$, $R^2$, $R^3$, $R^4$, $R^5$ and X are as above-mentioned.

Next, a compound of the general formula [I] wherein $R^6$ is lower alkyl group of carbon number 1–3 or benzyl group, i.e. a compound of a general formula [IV] can be produced by allowing a compound represented by the above-mentioned general formula [III] to react with halogenated lower alkyl or benzyl halide. Typically speaking, it can be produced by allowing a suitable alkyl halide, for example, methyl iodide, ethyl iodide etc. or benzyl halide to act on a compound of the general formula [III] in a suitable solvent, for example, dimethylformamide, dimethylsulfoxide, acetone, dioxane etc. and in the presence of a suitable base, for example, sodium carbonate, potassium carbonate, potassium bicarbonate etc. at room temperature or on heating with stirring.

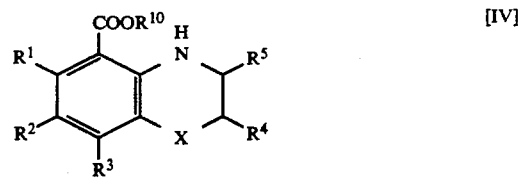

[IV]

wherein $R^1$, $R^2$, $R^3$, $R^4$, $R^5$ and X are as above-mentioned, $R^{10}$ denotes lower alkyl group or benzyl group.

Further, a compound of the general formula [III] can be produced by subjecting a compound of the general formula [IV] to hydrolysis or catalytic reduction. Typically speaking, in case $R^{10}$ is lower alkyl group of carbon number 1–3, it can be produced by hydrolizing a compound of the general formula [IV] in a suitable solvent, for example, methanol or ethanol etc. and in the presence of a suitable base, for example, sodium hydroxide or potassium hydroxide etc. at room temperature or on heating with stirring. In case $R^{10}$ is benzyl group, it can be produced by subjecting a compound of the general formula [IV] to catalytic reduction in a suitable solvent, for example, dimethylformamide etc. and in the presence of a suitable catalyst, for example, 10% palladium carbon.

Furthermore, a compound of the general formula [I] wherein X is —SO—$CHR^8$—$(CHR^9)m$—, i.e. a compound of the general formula [IV] can be produced by subjecting a compound of the general formula [I] wherein X is —SO—$CHR^8$—$(CHR^9)m$— or —$SO_2CH$-$R^8$—$(CHR^9)m$—, i.e. a compound of a general formula [V] to reduction. Typically speaking, it can be produced by subjecting a compound of the general formula [V] to reduction in a suitable solvent, for example, methanol, water or methylene chloride etc. with employing a suitable reducing agent, for example, stannous chloride, titanium trichloride or diphosphor tetraiodide etc., if circumstances require, sodium borohydride or lithium aluminum hydride etc. at room temperature or on heating with stirring.

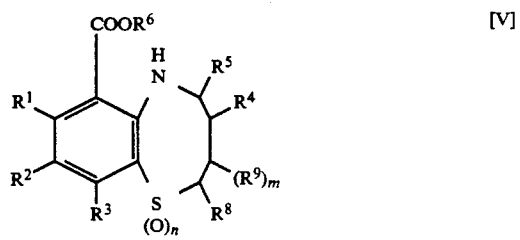

[V]

wherein $R^1$, $R^2$, $R^3$, $R^4$, $R^5$, $R^6$, $R^8$, $R^9$ and m are as above-mentioned, n denotes one or two.

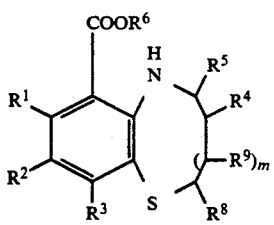

wherein $R^1$, $R^2$, $R^3$, $R^4$, $R^5$, $R^6$, $R^8$, $R^9$ and m are as above-mentioned.

Furthermore, a compound of the general formula [V] can be produced by oxidizing a compound of the general formula [VI]. Typically speaking, it can be produced by oxidizing a compound of the general formula [VI] in the presence of equal amount or excess amount of a mild oxidant, for example, m-chloroperbenzoic acid or aqueous solution of hydrogen peroxide etc. and in a suitable solvent, for example, methylene chloride, or alcohol etc. at room temperature or on heating with stirring.

Moreover, a compound of the general formula [I] wherein X is $-SO_2CHR^8-(CHR^9)m$, i.e. a compound of a general formula [VIII] can be prepared by oxidizing a compound of the general formula [I] wherein X is $SOCHR^8-(CHR^9)m$, i.e. a compound of a general formula [VII]. Typically speaking, it can be produced by oxidizing a compound of the general formula [VII] in the presence of equal amount or excess amount of a mild oxidant, for example, m-chloroperbenzoic acid or aqueous solution of hydrogen peroxide and in a suitable solvent, for example, methylene chloride or alcohol etc. at room temperature or on heating with stirring.

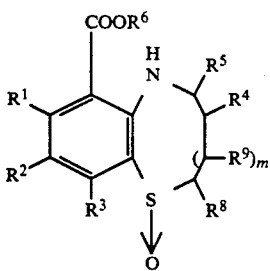

wherein $R^1$, $R^2$, $R^3$, $R^4$, $R^5$, $R^6$, $R^8$, $R^9$ and m are as above-mentioned.

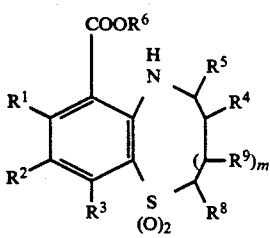

wherein $R^1$, $R^2$, $R^3$, $R^4$, $R^5$, $R^6$, $R^8$, $R^9$ and m are as above-mentioned.

Moreover, a compound of the general formula [I] wherein $R^2$ is amino group, i.e. a compound of a general formula [X] can be produced by subjecting a compound of the general formula [I] wherein $R^2$ is nitro group, i.e. a compound of a general formula [IX] to catalytic reduction. Typically speaking, it can be produced by subjecting a compound of the general formula [IX] to catalytic reduction in a suitable solvent, for example dimethylformamide etc. and in the presence of a suitable catalyst, for example, 10% palladium carbon.

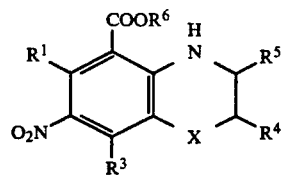

wherein $R^1$, $R^3$, $R^4$, $R^5$, $R^6$ and X are as above-mentioned.

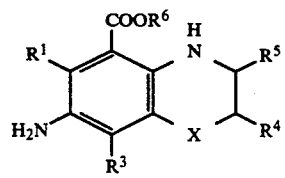

wherein $R^1$, $R^3$, $R^4$, $R^5$, $R^6$ and X are as above-mentioned.

Moreover, a compound of the general formula [I] wherein $R^2$ is lower alkanoylalkyl group of carbon number 1-3, benzoylamino group which can be substituted, lower alkylsufonylamino group of carbon number 1-3 or phenylsufonylamino group which can be substituted, i.e. a compound of a general formula [XII] can be prepared by acting a compound of the general formula [XI] on a compound of the general formula [I] wherein $R^2$ is amino group, i.e. a compound of the general formula [X]. Typically speaking, it can be produced by acting halogenide of the general formula [XI] on a compound of the general formula [X] in a suitable solvent, for example, dioxane, dimethylsulfoxide etc. and in the presence of a suitable base, for example, triethylamine, pyridine etc. with stirring at room temperature.

$$R^{11}-Y \qquad [XI]$$

wherein $R^{11}$ denotes lower alkanoyl group of carbon number 1-3, benzoyl group which can be substituted, lower alkylsulfonyl group of carbon number 1-3 or phenylsulfonyl group which can be substituted, Y denotes halogen atom.

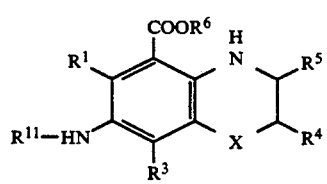

wherein $R^1$, $R^3$, $R^4$, $R^5$, $R^6$, $R^{11}$ and X are as above-mentioned.

Moreover, a compound of the general formula wherein $R^2$ is cyano group, i.e. a compound of a general formula [XIV] can be produced by acting cyanating agent on a compound of the general formula [I] wherein $R^2$ is bromine atom, i.e. a compound of a general formula [XIII]. Typically speaking, it can be produced by acting a suitable cyanating agent, for example, copper cyanide, potassium cyanide, sodium cyanide etc. on a compound of a general formula [XIII] in a suitable solvent, for example, dimethylformamide, pyridine, N-methylpyrrolidone on heating with stirring.

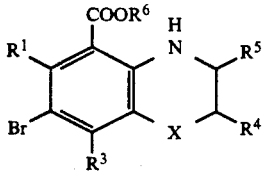

[XIII]

wherein $R^1$, $R^3$, $R^4$, $R^5$, $R^6$ and X are as above-mentioned.

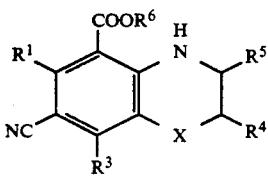

[XIV]

wherein $R^1$, $R^3$, $R^4$, $R^5$, $R^6$ and X are as above-mentioned.

Moreover, a compound of the general formula [I] wherein $R^2$ is carbomoyl group or carboxyl group, i.e. a compound of a general formula [XV] can be prepared by hydrolizing a compound of the general formula [I] wherein $R^2$ is cyano group, i.e. a compound of a general formula [XIV]. Typically speaking, it can be produced by hydrolizing a compound of the general formula [XIV] in a suitable solvent, for example, ethanol, methanol etc. with a suitable base, for example, sodium hydroxide, potassium hydroxide etc.

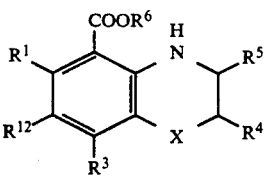

[XV]

wherein $R^1$, $R^3$, $R^4$, $R^5$, $R^5$ and X are as above-mentioned, $R^{12}$ denotes carbomoyl group or carboxyl group.

Moreover, a compound of the general formula [I] wherein $R^2$ is phenylethynyl group which can be substituted or ethynyl group which can be substituted, i.e. a compound of a general formula [XVII] can be produced by acting phenylacetylene which can be substituted or acetylene which can be substituted on a compound of a general formula [XVI]. Typically speaking, it can be produced by heating a compound of a general formula [XVI] and phenylacetylene which can be substituted or acetylene which can be substituted with triethylamine and copper iodide in a suitable solvent, for example, dimethylformamide, tetrahydrofuran etc. and in the presence of bis-triphenylphosphine palladium diacetate, bistriphenylphosphine palladium chloride etc.

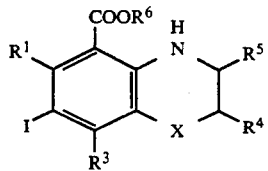

[XVI]

wherein $R^1$, $R^3$, $R^4$, $R^5$, $R^6$ and X are as above-mentioned.

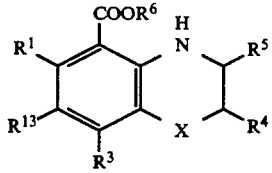

[XVII]

wherein $R^1$, $R^3$, $R^4$, $R^5$, $R^6$ and X are as above-mentioned, $R^{13}$ denotes phenylethynyl group which can be substituted, ethynyl group which can be substituted.

Moreover, a compound of the general formula [I] wherein $R^2$ is acetyl group or benzoylmethyl group which can be substituted, i.e. a compound of a general formula [XVIII] can be produced by subjecting a compound of the general formula [I] wherein $R^2$ is phenylethynyl group which can be substituted or ethynyl group which can be substituted, i.e. a compound of the general formula [XVII] to hydration. Typically speaking, it can be produced by heating a compound of the general formula [XVII] with concentrated sulfuric acid, mercuric sulfate etc. in a suitable solvent, for example, acetone containing water.

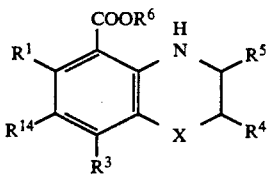

[XVIII]

wherein $R^1$, $R^3$, $R^4$, $R^5$, $R^6$ and X are as above-mentioned, $R^{14}$ denotes benzoylmethyl group, acetyl group.

Next, a compound represented by the general formula [I], if desired, can be converted into a salt thereof according to the conventional process. As an acid addition salt thereof, a salt of inorganic acid, for example, hydrochloric acid, sulfuric acid, phosphoric acid etc. or a salt of organic acid such as methansulfonic acid, lactic acid, acetic acid, citric acid, tartaric acid etc. can be exemplified. Then, as an alkali salt thereof, a metallic salt thereof such as sodium salt, potassium salt etc. can be exemplified.

THE BEST MODE TO EXECUTE THE PRESENT INVENTION

The concrete examples of the present invention are explained as follows, but the present invention suffers no restriction by these examples.

EXAMPLE 1

N-acetyl-7-amino-5-bromoindoline

To a mixed solution of ethanol (400 ml) and water (100 ml), were added N-acetyl-5-bromo-7-nitroindoline (133.1 g), iron powder (10 mesh; 75 g) and concentrated hydrochloric acid (5 ml), and the mixture was subjected to refluxing for 5 hours with vigorous stirring. The reaction mixture was filtered by suction while hot to remove insoluble matter, and then the filtrate thereof was concentrated and cooled on standing to give the intended compound 38.3 g (32.2%) as a brown needle crystal. M.P.: 154°–155° C.

EXAMPLE 2

N-acetyl-5-bromo-7-cyanoindoline

Into 6N hydrochloric acid (178.5 ml) was suspended N-acetyl-7-amino-5-bromoindoline (51.0 g), and aqueous solution (212 ml) of sodium nitrite (21.2 g) was dropwise added thereto under cooling with stirring over 30 minutes and at the inside temperature of not higher than −1° C. After stirred for 30 minutes at the temperature as such, sodium carbonate was added to the reaction mixture to neutralize it. This reaction mixture was poured into aqueous solution (200 ml) of copper cyanide (27.5 g) and sodium cyanide (30.7 g), and the mixture was allowed to stand for one night at room temperature. The reaction mixture was again subjected to stirring for 30 minutes at the inside temperature of 50° C. and was cooled to give a deposited crystal, which was then collected by filtration, washed with water and dried. The crude crystal was recrystallized from acetonitrile to give the intended compound 43.0 g (81.1%). M.P.: 170°–175° C.

EXAMPLE 3

5-Bromoindoline-7-carboxylic acid

After adding N-acetyl-5-bromo-7-cyano-indoline (17.7 g) to concentrated hydrochloric acid (177 ml), the mixture was subjected to refluxing for one hour with stirring. The reaction mixture was cooled with ice to give deposited crystal, which was then collected by filtration. The combined crystal and crude crystal obtained by concentrating the mother liquor were suspended into water (50 ml) to which thereafter 50% aqueous solution of sodium hydroxide was added, and then the insoluble matter was collected by filtration. To the filtrate was added concentrated hydrochloric acid, and the deposited crystal was collected by filtration. Further, after repeating this operation again, the obtained crystal was dried to give the intended compound 11.2 g (69.6%) as light yellow powder. M.P.: 212.5°–123.5° C. (decomp.)

Elementary analysis (%) as $C_9H_8BrNO_2$: Calculated value C: 44.66; H: 3.33; N: 5.79: Observed value C: 44.71; H: 3.24; N: 5.78.

EXAMPLE 4

N-Acetyl-7-cyano-5-nitroindoline

To a mixed solution of acetic acid (3.8 ml), concentrated sulfuric acid (4.7 ml) and funing nitric acid (0.8 ml), under cooling with stirring, were added only small portions of N-acetyl-7-cyano-indoline (2.42 g). After stirred at the temperature as such for 7.5 hours, the reaction mixture was poured into ice-water (50 ml). The deposited crystal was collected by filtration, washed with water and acetone, and then dried to give the intended compound 2.6 g (66.7%) as white powder. M.P.: 245°–255° C.

EXAMPLE 5

5-Nitroindoline-7-carboxylic acid

Into concentrated hydrochloric acid (63.6 ml) was dissolved N-acetyl-7-cyano-5-nitroindoline (5.3 g), which was then subjected to stirring at 140° C. for 45 minutes. The reaction mixture was cooled to 0° C. to give deposited crystal, which was then collected by filtration. The obtained crude crystal was suspended into water (50 ml), and was rendered basic by adding 50% sodium hydroxide, and the insoluble matter was collected by filtration. After adding concentrated hydrochloric acid to the filtrate, the deposited crystal was collected by filtration and dried to give the intended compound 3.7 g (77.1%) as yellow powder. M.P.: 294°–297° C. (decomp.)

Elementary analysis (%) as $C_9H_8N_2O_4$: Calculated value C: 51.93; H: 3.87; N: 13.46: Observed value C: 51.80; H: 3.83; N: 13.55.

EXAMPLE 6

4,5,6,7-Tetrahydroazepino[3,2,1-hi]indole-1,2-dione

To a solution of oxalic chloride (27.5 ml) in tetrahydrofuran (THF; 500 ml) which was subjected to refluxing with heating, was dropwise added a solution of 2,3,4,5-tetrahydro-1H-1-benzazepine (28.8 g) in THF (100 ml), which was thereafter subjected to stirring for 4 hours as such. After cooled, the solvent was distilled off and the residue was dissolved into carbon disulfide (600 ml), to which then only small portions of aluminium chloride (52.27 g) were added at room temperature with stirring and was further subjected to stirring for 4 hours. With removal of supernatant solution from the reaction mixture, ice-water was added to the residue, which was then extracted with chloroform. The organic layer was thoroughly washed with water, dried over anhydrous sodium sulfate and then the solvent thereof was distilled off.

The residue was recrystallized from acetonitril to give the intended compound 28.32 g (71.9%) as dark red crystal. M.P.: 132° C.

Elementary analysis (%) as $C_{12}H_{11}NO_2$: Calculated value C: 71.63; H: 5.51; N: 6.96: Observed value C: 72.10; H: 5.63; N: 7.05.

EXAMPLE 7

9-Bromo-4,5,6,7-Tetrahydroazepino[3,2,1-hi]indole-1,2-dione 4,5,6,7-Tetrahydroazepino[3,2,1-hi]indole-1,2-dione (10 g) and N-bromosuccinic imide (11.17 g) were dissolved into dimethylformamide (DMF; 10 ml) and, after stirred for one hour at 80° C., the solvent was distilled off. The residue was dissolved into chloroform, washed with water, dried over anhydrous sodium sulfate and thereafter the solvent was distilled off to give the intended compound 13.99 g (95.5%), which was then recrystallized from acetonitril to give dark red needle crystal. M.P.: 159°–160° C.

Elementary analysis (%) as $C_{12}H_{10}BrNO_2$: Calculated value C: 51.45; H: 3.60; N: 5.00: Observed value C: 51.33; H: 3.56; N: 5.10.

EXAMPLE 8

9-Nitro-4,5,6,7-Tetrahydroazepino[3,2,1-hi]indole-1,2-dione

After 2,3,4,5-tetrahydro-1H-1-benzazepine (3.42 g) was added under cooling with ice to fuming nitric acid (8 ml) and the mixture was subjected to stirring for one hour at the same temperature, the temperature thereof was put back to room temperature and the mixture was stirred for one hour. The reaction mixture was poured into ice-water (100 ml), and the deposited crystal was collected by filtration, washed with water and dried to give the intented compound 3.97 g (90%), which was then recrystallized from acetonitril to give orange color crystal. M.P.: 153°–154° C.

Elementary analysis (%) as $C_{12}H_{10}N_2O_4$: Calculated value C: 58.54; H: 4.09; N: 11.38: Observed value C: 58.56; H: 4.06; N: 11.37.

EXAMPLE 9

7-Bromo2,3,4,5-tetrahydro-1H-1-benzazepine-9-carboxylic acid

9-Bromo-4,5,6,7-tetrahydroazepino[3,2,1-hi]indole-1,2-dione (13.99 g) and sodium hydroxide (10 g) were dissolved into water (800 ml), to which then 35% aqueous solution of hydrogen peroxide (10 ml) was added, and the mixture was stirred for 4 hours at room temperature. The mixture was rendered to have pH 2 with concentrated hydrochloric acid, and the deposited crystal was collected by filtration, washed with water and dried to give the intended compound 10.24 (76.4%), which was then recrystallized from ethyl acetate-n-hexane to give yellow needle crystal. M.P.: 157°–158° C.

Elementary analysis (%) as $C_{11}H_{12}BrNO_2$: Calculated value C: 48.91; H: 4.48; N: 5.19: Observed value C: 48.62; H: 4.40; N: 5.12.

EXAMPLE 10

7-Nitro-2,3,4,5-tetrahydro-1H-1-benzazepine-9-carboxylic acid

Likewise as in Example 9, the intended compound was obtained in yield of 80.6% from 9-nitro-4,5,6,7-tetrahydroazepino(3,2,1-hi)indole-1,2-dione. M.P.: 224°–225° C.

Elementary analysis (%) as $C_{11}H_{12}N_2O_4$: Calculated value C: 55.93; H: 5.12; N: 11.86: Observed value C: 55.88; H: 5.15; N: 11.83.

EXAMPLE 11

7-Cyano-2,3,4,5-tetrahydro-1H-1-benzazepine-9-carboxylic acid a) 7-Bromo-2,3,4,5-tetrahydro-1H-1-benzazepine-9-carboxylic acid benzyl ester To 7-bromo-2,3,4,5-tetrahydro-1H-1-benzazepine-9-carboxylic acid (8.53 g) dissolved in DMF (80 ml), were added potassium carbonate (13.8 g) and benzyl bromide (4.5 ml) and the mixture was stirred for 2 hours at room temperature. After the insoluble matter was filtered off and the filtrate was concentrated, a mixed liquid of ethyl acetate-benzene (1:1, 400 ml) was added to the residue, and the mixture was washed with water, dried over anhydrous sodium sulfate and then subjected to distilling off the solvent to give the intended compound 11.35 g (99.7%) as brown oily matter.

b) 7-Cyano-2,3,4,5-tetrahydro-1H-1-benzazepine-9-carboxylic acid benzyl ester The ester compound (11.35 g) obtained in a) was dissolved in DMF (40 ml), added with cuprous cyanide (3.75 g), and the mixture was refluxed for 8 hours. After cooled, ferrous chloride.6 hydrate (10 g), water (100 ml) and concentrated hydrochloric acid (2 ml) were added to the reaction mixture, which was then stirred for 30 minutes at 60° C. and extracted with ethyl acetate. The organic layer was washed successively with water, 10% hydrochloric acid, water, 5% aqueous solution of sodium hydroxide and water, and dried over anhydrous sodium sulfate, which was thereafter subjected to distilling off the solvent. The residue was purified through silica-gel column-chromatography (developing solvent; ethyl acetate: n-hexane=1:3) to give the intended compound 6.81 g (70.6%) as light yellow crystal.

c) 7-Cyano-2,3,4,5-tetrahydro-1H-1-benzazepine-9-carboxylic acid

The compound (3.30 g) obtained in b) was dissolved into ethanol (200 ml), to which then 10% palladium-carbon (500 mg) was added, and was subjected to catalytic reduction at room temperature. After 4 hours, the catalyst was filtered off and the filtrate was concentrated to give the intended compound 1.87 g (94%), which was then recrystallized from ethyl acetate-n-hexane to give slightly yellow crystal. M.P.: 175° C.

Elementary analysis (%) as $C_{12}H_{12}N_2O_2$: Calculated value C: 66.65; H: 5.59; N: 12.95; Observed value C: 66.73; H: 5.62; N: 12.93.

EXAMPLE 12

2,3,4,5-Tetrahydro-1H-1-benzazepine-7,9-di-carboxylic acid

7-Cyano-2,3,4,5-tetrahydro-1H-1-benzazepine-9-carboxylic acid benzyl ester (3.30 g) and sodium hydroxide (2 g) in a mixed solution of water-ethanol (1:1, 60 ml) was refluxed for 8 hours. After cooled, water (100 ml) was added to the reaction mixture, which was then rendered to have $_p$H 3 with concentrated hydrochloric acid. The deposited crystal was collected by filtration, washed with water and dried to give the intended compound 1.84 g (85.0%), which was then recrystallized from ethanol to give slightly yellow crystal. M.P.: 287°–288° C.

Elementary analysis (%) as $C_{12}H_{13}NO_4$: Calculated value C: 61.27; H: 5.57; N: 5.95; Observed value C: 61.29; H: 5.58; N: 6.43.

EXAMPLE 13

7-Methansulfonylamino-2,3,4,5-tetrahydro-1H-1-benzazepine-9-carboxylic acid a) 7-Nitro-2,3,4,5-tetrahydro-1H-1-benzazepine-9-carboxylic acid methyl ester 7-Nitro-2,3,4,5-tetrahydro-1H-1-benzazepine-9-carboxylic acid (6.25 g) was dissolved into DMF (50 ml), to which then potassium carbonate (11 g) and methyl iodide (4.9 ml) were added, and was stirred for 2 hours at room temperature. After the insoluble matter was filtered off and the filtrate was concentrated. ethyl acetate (500 ml) was added to the residue, which was then washed with water and dried over anhydrous sodium sulfate. The solvent was distilled off to give the intended compound 6.65 g (quantitatively) as yellow crystal.

b)
7-Amino-2,3,4,5-tetrahydro-H-1-benzazepine-9-carboxylic acid methyl ester The ester (6.65 g) obtained in a ) was dissolved into DMF (200 ml), to which 10% palladium-carbon (1 g) was then added, and was subjected to catalytic reduction at room temperature. After 7 hours, the catalyst was filtered of and the filtrate was concentrated to give the intended compound 5.86 g (quantitatively) as brown oily matter.

c)
7-Methanesulfonylamino-2,3,4,5-tetrahydro-1H-1-benzazepine-9-carboxylic acid methyl ester The ester (2.90 g) obtained in b), mesil chloride (MsCl, 1.4 ml) and triethyl amino (2.5 ml) were dissolved in doxane (80 ml), and the resultant solution was stirred for 6 hours at room temperature. Water (300 ml) was added to the reaction mixture, which was then extracted with ethyl acetate, dried over anhydrous sodium sulfate and subjected to distilling off the solvent to give the intended compound 2.94 g (80.8%) as brown oil matter.

d)
7-Methanesulfonylamino-2,3,4,5-tetrahydro-1H-1-benzazepine-9-carboxylic acid The ester (2.94 g) obtained in c) and sodium hydroxide (2 g) were dissolved into a mixed solution of water-ethanol (1:1, 50 ml), and was refluxed for 4 hours. To the reaction mixture was added water (200 ml), Which was then rendered to have pH 2 and extracted with ethyl acetate. The organic layer was washed with water, dried over anhydrous sodium sulfate and the solvent was distilled off to give the intended compound 1.48 g (50.3%), which was then recrystallized from ethanol to give yellow crystal. M.P.: 204°–205° C.

Elementary analysis (%) as $C_{12}H_{16}N_2O_4S$: Calculated value C: 50.69; H: 5.67; N: 9.85; Observed value C: 50.43; H; 5.65; N: 9.60.

EXAMPLE 14
7-p-Toluenesulfonylamino-2,3,4,5-tetrahydro-1H-1-benzazepine-9-carboxylic acid a)
7-Toluenesulfonylamino-2,3,4,5-tetrahydro-1H-1-benzazepine-9-carboxylic acid methyl ester Employing 7-amino-2,3,4,5-tetrahydro-1H-1-benzazepine-9-carboxylic acid methyl ester with employment of p-tosyl chloride, which were allowed to react likewise as in Example 13 c), the intended compound was obtained in yield of 95.0% as brown oily matter.

b)
7-p-Toluenesulfonylamino-2,3,4,5-tetrahydro-1H-1-benzazepine-9-carboxylic acid The compound obtained in a) was allowed to react likewise as in Example 10 d) to give the intended compound in yield of 87.7%, which was then recrystallized from ethanol to give slightly yellow crystal. M.P.: 232°–233° C.

Elementary analysis (%) as $C_{18}H_{20}N_2O_4S$: Calculated value C: 59.98; H: 5.59; N: 7.77; Observed value C: 60.09; H: 5.62; N: 7.85.

With respect to the compound of the present invention, the results supporting the utility thereof are shown by the Experimental examples as follows.

EXPERIMENTAL EXAMPLE 1

Inhibition of increased vascular permeability

Male ddy mice (6 weeks of age) were used in this experiment. Example 9 compound suspended in 5% gum arabic solution was administered p.o., 45 minutes before the i.v. injection of 1.0% Evans blue solution (0.1 ml/10 g B.W.). Immediately after the i.v. injection, 1.0% acetic acid solution was administered i.p. (0.1 ml/10 g B.W.). The mice were killed 30 minutes after the acetic acid injection. Peritoneal exudate was collected by washing out the peritoneal cavity with physiological saline and centrifuged at 3,000 r.p.m. After the centrifugation, spectrophotometry of the supernatant was measured at 630 nm. Results were expressed as dye leakage and percent inhibition.

TABLE 1

| Compound | Dose (mg/kg) | N | Dye leakage ($\mu$g/ml) (mean ± S.E | Inhibition (%) |
|---|---|---|---|---|
| Control | — | 8 | 25.77 ± 1.81 | — |
| Example 9 | 100 | 9 | 17.43 ± 1.38* | 32.3 |

*Significantly different from control, $p < 0.01$.

As shown in Table 1, the compound of the present invention significantly inhibited the rise in vascular permeability caused by the injection of acetic acid.

EXPERIMENTAL EXAMPLE 2

Inhibitory action against thermal denaturation of protein

Bovine serum albumin was dissolved into 1/15M phosphoric acid buffer solution, which was then adjusted to 0.7%. After adding the solution of the present invention compound thereto, it was heated at 65° C. for 7-8 minutes. After cooled, the absorbance at 660 nm was measured, compared with the absorbance of the reference to derive the inhibitory rate and then the concentration necessary to inhibit 50% was obtained.

TABLE 2

| | $IC_{50}$ ($\mu$M) |
|---|---|
| Example 9 | 132 |
| Example 10 | 71 |

As shown in Table 2, the inhibitory action against thermal denaturation of protein was obtained in the present invention compound.

EXPERIMENTAL EXAMPLE 3

Inhibitory action against bone resorption

According to Raisz et al method (J. Clin. Invest., 155, 103 (1965)), bone piece of front arm of mouse labelled with radioactive calcium ($^{45}$Ca) was prepared in order to measure bone resorption. That is, the radioactive calcium ($^{45}CaCl_2$; 200 $\mu$Ci) was injected under the skin to the back of rats in the 17th day of pregnancy and two days later they were killed with exsanguination by cutting of the carotid artery thereof. After the embryos were picked up and washed with sterilized phosphated buffer solution, the bone of front arm was taken out, which was then rendered free of the attached muscle and cartilage of the both ends, and said piece of bone was cultivated in the culture medium of BGJb.

Next, according to the method of Tsuda et al (J. Bone Miner. Metab., 1, 207 (1986)), the effect of the present invention compound against the bone resorption was determined, which are described as follows.

The piece of bone was put on a milipore-filter, and was pre-cultivated, in a well with 24 holes plate accomodating 0.6 ml culture medium of BGJb, at 37° C. and under 5% carbon dioxide. After the precultivation for 24 hours, said bone with the filter were transferred into a test culture medium added with interleukin-1β (1L-1β) or with both 1L-1β and drugs and the cultivation was continued. After 72 hours cultivation in said test culture medium, 0.3 ml of the supernatant was taken out and $^{45}$Ca released from the piece of bone was determined. After the piece of bone was immersed in 0.3 ml of 1N hydrochloric acid for more than 1.5 hours, 10 ml of ACSII was added thereto and the radioactivity was determined. Furthermore, the activity of bone resorption was represented by the ratio (percentage) of $^{45}$Ca released in the supernatant of cultivation to the total radioactivity which had been contained in the piece of bone (the sum of radioactivities in the piece of bone and the supernatant of cultivation). One well with 24 holes plate was employed per one piece of bone and every experimental group was constituted by 5-6 pieces of bone of embryo obtained from one pregnant rat.

The inhibitory rate against bone resorption was derived from the following formula.

Inhibitory rate (%) =

$$\frac{(\text{activity of 1L-1}\beta \text{ addition group}) - (\text{activity of both 1L-1}\beta \text{ and drugs addition group})}{(\text{activity of 1L-1}\beta \text{ addition group}) - (\text{activity of non-addition (reference) group})} \times 100$$

The result was illustrated in Table 3.

TABLE 3

| | Concentration (μg/ml) | Inhibitory rate against bone resorption (%) |
|---|---|---|
| Example 11 c) | 25 | 54 |
| Example 12 | 25 | 84 |
| Ipriflavone* | 25 | 58 |

*7-isopropoxy isoflavone

As obvious from the above, the present invention compound has a strong inhibotory action against bone resorption.

Utilizability on industrial field

As stated above, the cyclic anthranilic acid derivatives of the present invention have the immunomodulating action and the strong inducing ability of suppresor T cell as well as curing effect to rheumatic arthritis, and are further suitable for a curing medicament of metabolic bone diseases.

We claim:

1. Compounds represented by the following formula

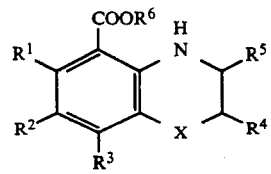

wherein $R^1$, $R^2$ and $R^3$, being the same or different from each other, denote hydrogen, halogen, lower alkyl group of 1-3 carbons, lower alkoxy group of 1-3 carbons, amino group, nitro group, hydroxyl group, sulfonamide group, trifluoromethyl group, cyano group, carboxyl group, carbamoyl group, acetyl group, benzoyl-methyl group which can be substituted with one to three halogen, lower alkyl, lower alkoxy, or hydroxy groups, methylthio group, phenylethynyl group which can be substituted with one to three halogen, lower alkyl, lower alkoxy or hydroxy groups, ethynyl group which can be substituted with one to three halogen, lower alkyl, lower alkoxy or hydroxy groups, lower alkanoyl-amino group of 1-3 carbons, benzoyl-amino group which can be substituted with one to three halogen, lower alkyl, lower alkoxy or hydroxy groups, lower alkylsulfonylamino group of 1-3 carbons or phenylsulfonylamino group which can be substituted with one to three halogen, lower alkyl, lower alkoxy or hydroxy groups, $R^4$ or $R^5$, being the same or different from each other, denotes hydrogen, lower alkyl group of 1-3 carbons, cyano group, carboxyl group, hydroxymethyl group, phenyl group which can be substituted with one to three halogen, lower alkyl, lower alkoxy or hydroxy groups or benzyl group which can be substituted with one to three halogen, lower alkyl, lower alkoxy or hydroxy groups, $R^6$ denotes hydrogen atom, lower alkyl group of 1-3 carbons or benzyl group, x denotes —$CHR^7$—$CHR^8$—$(CHR^9)_m$—, —O—$CHR^8$—$(CHR^9)_m$—, —$S(O)_n$—$CHR^8$—$(CHR^9)_m$— or —$CO$—$(CHR^8)_p$—$(CHR^9)_m$—, wherein $R^7$, $R^8$ or $R^9$, being the same or different from each other, denote hydrogen, lower alkyl group of 1-3 carbons, cyano group, carboxyl group, hydroxymethyl group or phenyl group which can be substituted with one to three halogen, lower alkyl, lower alkoxy or hydroxy groups, m or p denotes 0 or 1 respectively, and n denotes an integer of 0-2, provided $R^2$ can not be chlorine or hydrogen when both $R^7$ and $R^8$ are hydrogen and m is equal to 0.

2. Antirheumatic drug, autoimmune disease curing drug and metabolic bone disease curing drug, comprising at least one compound represented by the following formula as an active ingredient

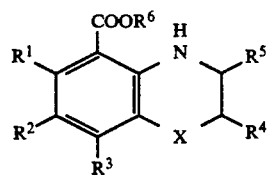

wherein $R^1$, $R^2$ and $R^3$, being the same or different from each other, denote hydrogen, halogen, lower alkyl group of 1-3 carbons, lower alkoxy group of 1-3 carbons, amino group, nitro group, hydroxyl group, sulfonamide group, trifluoromethyl group, cyano group, carboxyl group, carbamoyl group, acetyl group, benzoyl-methyl group which can be substituted with one to three halogen, lower alkyl, lower alkoxy, or hydroxy groups, methylthio group, phenylethynyl group which can be substituted with one to three halogen, lower alkyl, lower alkoxy or hydroxy groups, ethynyl group which can be substituted with one to three halogen, lower alkyl, lower alkoxy or hydroxy groups, lower alkanoyl-amino group of 1-3 carbons, benzoyl-amino group which can be substituted with one to three halogen, lower alkyl, lower alkoxy or hydroxy groups, lower alkylsulfonylamino group of 1-3 carbons or phenylsulfonylamino group which can be substituted with one to three halogen, lower alkyl, lower alkoxy or hydroxy groups, $R^4$ or $R^5$, being the same or different from each other, denotes hydrogen, lower alkyl group of 1-3 carbons, cyano group, carboxyl group, hydroxymethyl group, phenyl group which can be substituted with one to three halogen, lower alkyl, lower alkoxy or hydroxy groups or benzyl group which can be substituted with one to three halogen, lower alkyl, lower alkoxy or hydroxy groups, $R^6$ denotes hydrogen atom, lower alkyl group of 1-3 carbons or benzyl group, x denotes $—CHR^7—CHR^8—(CHR^9)_m—$, $—O—CHR^8—(CHR^9)_m—$, $—S(O)_n—CHR^8—(CHR^9)_m—$ or $—CO—(CHR^8)_p—(CHR^9)_m—$, wherein $R^7$, $R^8$ or $R^9$, being the same or different from each other, denote hydrogen, lower alkyl group of 1-3 carbons, cyano group, carboxyl group, hydroxymethyl group or phenyl group which can be substituted with one to three halogen, lower alkyl, lower alkoxy or hydroxy groups, m or p denotes 0 or 1 respectively, and n denotes an integer of 0-2, provided $R^2$ can not be chlorine or hydrogen when both $R^7$ and $R^8$ are hydrogen and m is equal to 0.

* * * * *